US011432803B2

(12) United States Patent
Perrey et al.

(10) Patent No.: US 11,432,803 B2
(45) Date of Patent: Sep. 6, 2022

(54) METHOD AND SYSTEM FOR GENERATING A VISUALIZATION PLANE FROM 3D ULTRASOUND DATA

(71) Applicant: General Electric Company, Wauwatosa, WI (US)

(72) Inventors: Christian Fritz Perrey, Zipf (AT); Suvadip Mukherjee, Bangalore (IN); Nitin Singhal, Bangalore (IN); Rakesh Mullick, Bangalore (IN)

(73) Assignee: General Electric Company, Schenectady, NY (US)

(*) Notice: Subject to any disclaimer, the term of this patent is extended or adjusted under 35 U.S.C. 154(b) by 338 days.

(21) Appl. No.: 16/523,098

(22) Filed: Jul. 26, 2019

(65) Prior Publication Data
US 2019/0343487 A1 Nov. 14, 2019

Related U.S. Application Data

(63) Continuation of application No. 15/258,099, filed on Sep. 7, 2016, now abandoned.

(51) Int. Cl.
A61B 8/08 (2006.01)
G01S 15/89 (2006.01)
(Continued)

(52) U.S. Cl.
CPC .............. A61B 8/483 (2013.01); A61B 8/085 (2013.01); A61B 8/469 (2013.01);
(Continued)

(58) Field of Classification Search
CPC ....... A61B 8/483; A61B 8/085; A61B 8/4427; A61B 8/466; A61B 8/5207; A61B 8/565; G01S 7/52068; G01S 15/8993
See application file for complete search history.

(56) References Cited

U.S. PATENT DOCUMENTS 5,287,273 A * 2/1994 Kupfer ................... G16H 10/40
600/431
8,879,813 B1 * 11/2014 Solanki ..................... A61B 3/14
382/128
(Continued)

FOREIGN PATENT DOCUMENTS

EP 0219435 A2 * 4/1987 ............... G06T 7/12

OTHER PUBLICATIONS

Sofka et al., Automatic Detection and Measurement of Structures in Fetal Head Ultrasound Volumes Using Sequential Estimation and Integrated Detection Network, IEEE Transactions on Medical Imaging vol. 33, No. 5, May 2014 (Year: 2014).*
(Continued)

Primary Examiner — Amelie R Davis
Assistant Examiner — John Denny Li

(57) ABSTRACT

A system (e.g., an ultrasound imaging system) is provided. The system includes an ultrasound probe configured to acquire three-dimensional (3D) ultrasound data of a volumetric region of interest (ROI). The system further includes a display, a memory configured to store programmed instructions, and a controller circuit. The controller circuit includes one or more processors. The controller circuit is configured to execute the programmed instructions stored in the memory. When executing the programmed instructions, the controller circuit performs a plurality of operations. The operations includes collecting the 3D ultrasound data from an ultrasound probe and identifying a select set of the 3D ultrasound data corresponding to an object of interest within the volumetric ROI. The operations further include segmenting the object of interest from the select set of the 3D ultrasound data, generating a visualization plane of the object of interest, and displaying the visualization plane on the display.

20 Claims, 11 Drawing Sheets

(51) Int. Cl.
*G01S 7/52* (2006.01)
*A61B 8/00* (2006.01)

(52) U.S. Cl.
CPC ...... *G01S 7/52068* (2013.01); *G01S 15/8993* (2013.01); *A61B 8/4427* (2013.01); *A61B 8/466* (2013.01); *A61B 8/5207* (2013.01); *A61B 8/565* (2013.01)

(56) References Cited

U.S. PATENT DOCUMENTS

| | | | | |
|---|---|---|---|---|
| 2007/0161905 | A1* | 7/2007 | Munrow | G01S 15/8918 |
| | | | | 600/459 |
| 2008/0146932 | A1* | 6/2008 | Chalana | A61B 8/0866 |
| | | | | 600/447 |
| 2009/0076387 | A1* | 3/2009 | Simopoulos | A61B 8/483 |
| | | | | 600/437 |
| 2009/0182234 | A1* | 7/2009 | Perrey | A61B 8/0825 |
| | | | | 600/443 |
| 2016/0078615 | A1* | 3/2016 | Zhan | G06T 15/00 |
| | | | | 382/128 |

OTHER PUBLICATIONS

Machine Translation of EP-0219435-A2 (Year: 1987).*

* cited by examiner

मेथड AND SYSTEM FOR GENERATING A VISUALIZATION PLANE FROM 3D ULTRASOUND DATA

METHOD AND SYSTEM FOR GENERATING A VISUALIZATION PLANE FROM 3D ULTRASOUND DATA

CROSS-REFERENCE TO RELATED APPLICATIONS

The present application is a continuation of and claims priority to U.S. patent application Ser. No. 15/258,099, entitled "Method and System for Generating a Visualization Plane From 3D Ultrasound Data", and filed on Sep. 7, 2016, the entire subject matter of which is incorporated herein by reference in its entirety.

FIELD

Embodiments described herein generally relate to generating a visualization plane of an object of interest from an ultrasound volume for a diagnostic medical imaging system.

BACKGROUND OF THE INVENTION

Diagnostic medical imaging systems typically include a scan portion and a control portion having a display. For example, ultrasound imaging systems usually include ultrasound scanning devices, such as ultrasound probes having transducers that are connected to an ultrasound system to control the acquisition of ultrasound data by performing various ultrasound scans (e.g., imaging a volume or body).

The ultrasound systems are controllable to operate in different modes of operation to perform different scans, for example, to view anatomical structures within the patient such as an endometrium cavity to diagnose malformations of the uterus (e.g., septate, bicornuate uterus, unicornuate uterus). Conventional ultrasound imaging systems require the user or technician having high ultrasound expertise to manually align three-dimensional (3D) ultrasound data along three orthogonal two-dimensional (2D) planes. A mid-coronal plane is defined and visualized based on the 2D planes, which is utilized to determine a shape of the endometrium cavity. Due to the extensive manual interaction to identify the 2D mid-coronal plane, the diagnosis is susceptible to operator variability. Additionally, the visualization along the mid-coronal plane is static, and may not accurately represent the uterus. Various embodiments disclosed herein may address one or more of the challenges set forth above.

BRIEF DESCRIPTION OF THE INVENTION

In an embodiment, a method (e.g., for generating a visualization plane of an object of interest from an ultrasound volume) is provided. The method includes acquiring three-dimensional (3D) ultrasound data of a volumetric region of interest (ROI) from an ultrasound probe, and identifying a select set of the 3D ultrasound data corresponding to an object of interest within the volumetric ROI. The method further includes segmenting the object of interest from the select set of the 3D ultrasound data, generating a visualization plane of the object of interest, and displaying the visualization plane on a display.

In another embodiment a system (e.g., an ultrasound imaging system) is provided. The system includes an ultrasound probe configured to acquire three-dimensional (3D) ultrasound data of a volumetric region of interest (ROI). The system further includes a display, a memory configured to store programmed instructions, and a controller circuit. The controller circuit includes one or more processors. The controller circuit is configured to execute the programmed instructions stored in the memory. When executing the programmed instructions, the controller circuit performs a plurality of operations. The operations includes collecting the 3D ultrasound data from an ultrasound probe and identifying a select set of the 3D ultrasound data corresponding to an object of interest within the volumetric ROI. The operations further include segmenting the object of interest from the select set of the 3D ultrasound data, generating a visualization plane of the object of interest, and displaying the visualization plane on the display.

In another embodiment, a tangible and non-transitory computer readable medium having one or more computer software modules is provided. The software modules are configured to direct one or more processors to acquire three-dimensional (3D) ultrasound data of a volumetric region of interest (ROI) from an ultrasound probe, identify a select set of the 3D ultrasound data corresponding to an object of interest within the volumetric ROI, segment the object of interest from the select set of the 3D ultrasound data, generate a visualization plane of the object of interest, and display the visualization plane on a display.

DETAILED DESCRIPTION OF THE INVENTION

Figure 1:
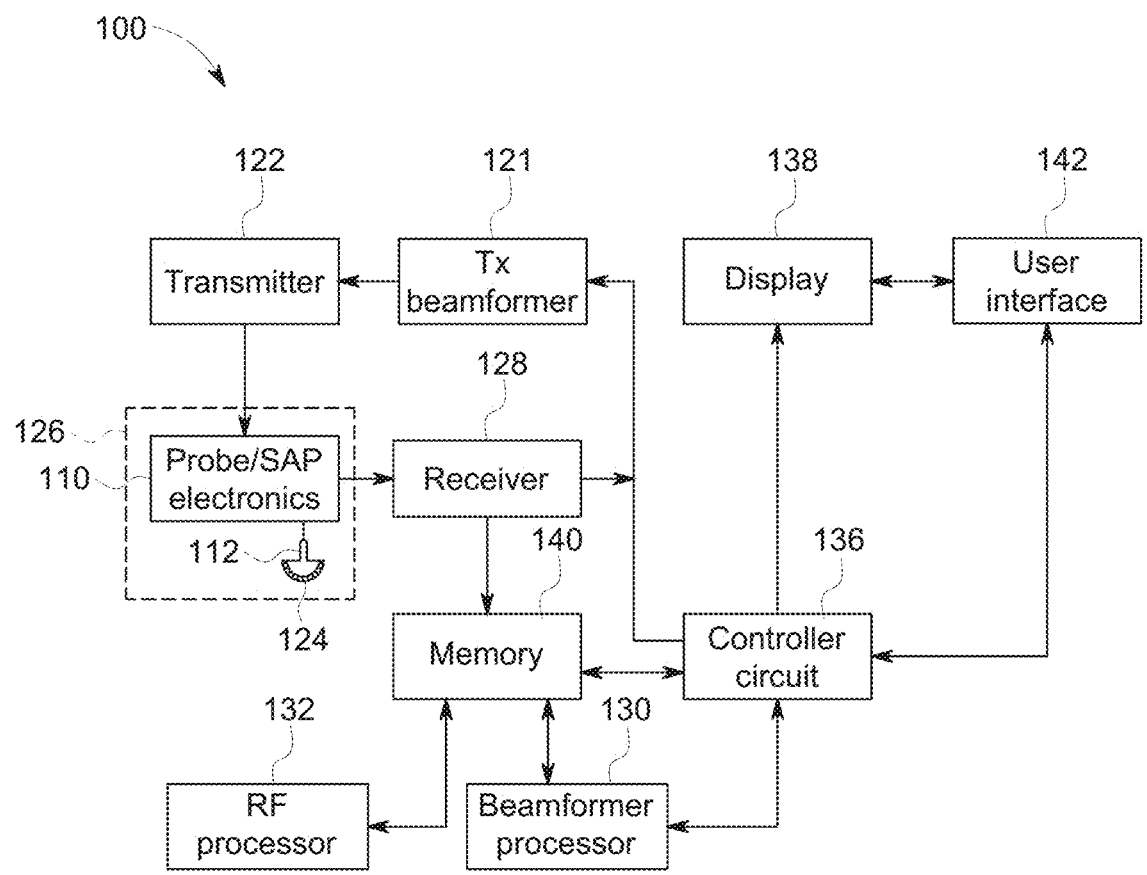
FIG. 1 illustrates a schematic block diagram of an ultrasound imaging system, in accordance with an embodiment.

The following detailed description of certain embodiments will be better understood when read in conjunction with the appended drawings. To the extent that the figures illustrate diagrams of the functional modules of various embodiments, the functional blocks are not necessarily indicative of the division between hardware circuitry. Thus, for example, one or more of the functional blocks (e.g., processors or memories) may be implemented in a single piece of hardware (e.g., a general purpose signal processor or a block of random access memory, hard disk, or the like). Similarly, the programs may be stand-alone programs, may be incorporated as subroutines in an operating system, may be functions in an installed software package, and the like.

It should be understood that the various embodiments are not limited to the arrangements and instrumentality shown in the drawings.

As used herein, an element or step recited in the singular and proceeded with the word "a" or "an" should be understood as not excluding plural of said elements or steps, unless such exclusion is explicitly stated. Furthermore, references to "one embodiment" of the present invention are not intended to be interpreted as excluding the existence of additional embodiments that also incorporate the recited features. Moreover, unless explicitly stated to the contrary, embodiments "comprising" or "having" an element or a plurality of elements having a particular property may include additional elements not having that property.

Various embodiments provide systems and methods for an automated workflow to localize, segment, and visualize a plane of an object of interest based on an ultrasound volume. For example, the object of interest may represent an anatomical structure, such as a cavity (e.g., an endometrium cavity), organ, blood vessel, and/or the like within 3D ultrasound data of a volumetric region of interest. The localization of the object of interest may be based on a learning based object detection framework to identify a structure of the object of interest within a two-dimensional (2D) slice of the 3D ultrasound data. The identified structure of the object of interest is utilized to initialize a 3D segmentation procedure using deformable models, which can be visualized as a 3D visualization of the object of interest. Based on the 3D visualization, malformations (e.g., uterine malformations) of the object of interest can be identified based on an overall shape of the object of interest represented as the 3D visualization. Additionally or alternatively, a visualization plane of the object of interest can be calculated using a least square surface fitting technique. For example, the visualization plane may correspond to a mid-coronal surface of the uterine cavity. The visualization plane may be visualized using a texture mapping algorithm, which highlights the morphology and structure of the object of interest at different axes.

A technical effect of at least one embodiment described herein reduces operator dependency by performing automated alignments and reduces procedure times. A technical effect of at least one embodiment described herein enhances the diagnostic accuracy. A technical effect of at least one embodiment described herein enables the user to visualize a visualization plane, such as a mid-coronal plane, from multiple views. A technical effect of at least one embodiment described herein allows a user to visualize and identify structural deformations in 3D, which may not be accurately represented in a 2D projection used in conventional diagnostic medical imaging systems.

FIG. 1 is a schematic diagram of a diagnostic medical imaging system, specifically, an ultrasound imaging system 100. The ultrasound imaging system 100 includes an ultrasound probe 126 having a transmitter 122 and probe/SAP electronics 110. Optionally, the ultrasound probe 126 may be an intra-cavity ultrasound probe configured to acquire ultrasound data or information within an object of interest, such as a cavity (e.g., vaginal cavity, uterine cavity, ear canal, rectal cavity, endometrium cavity, and/or the like) proximate to and/or containing a region of interest (e.g., organ, blood vessel, uterus, and/or the like) of the patient for generating one or more ultrasound images.

The ultrasound probe 126 is communicatively coupled to the controller circuit 136 via the transmitter 122. The transmitter 122 transmits a signal to a transmit beamformer 121 based on acquisition settings received by the user. The signal transmitted by the transmitter 122 in turn drives the transducer elements 124 within the transducer array 112. The transducer elements 124 emit pulsed ultrasonic signals into a patient (e.g., a body). The transducer array 112 may have a variety of array geometries and configurations for the transducer elements 124 which may be provided as part of, for example, different types of ultrasound probes 126. Further, the array 112 of transducer elements 124 may be provided as part of, for example, different types of ultrasound probes. Optionally, the ultrasound probe 126 may include one or more tactile buttons (not shown).

The acquisition settings may define an amplitude, pulse width, frequency, and/or the like of the ultrasonic pulses emitted by the transducer elements 124. The acquisition settings may be adjusted by the user by selecting a gain setting, power, time gain compensation (TGC), resolution, and/or the like from the user interface 142.

The transducer elements 124, for example piezoelectric crystals, emit pulsed ultrasonic signals into a body (e.g., patient) or volume corresponding to the acquisition settings along one or more scan planes. The ultrasonic signals may include, for example, one or more reference pulses, one or more pushing pulses (e.g., shear-waves), and/or one or more pulsed wave Doppler pulses. At least a portion of the pulsed ultrasonic signals back-scatter from the region of interest (ROI) to produce echoes. The echoes are delayed in time and/or frequency according to a depth or movement, and are received by the transducer elements 124 within the transducer array 112. The ultrasonic signals may be used for imaging, for generating and/or tracking shear-waves, for measuring changes in position or velocity within the ROI, differences in compression displacement of the tissue (e.g., strain), and/or for therapy, among other uses.

The probe/SAP electronics 110 may be used to control the switching of the transducer elements 124. The probe/SAP electronics 110 may also be used to group the transducer elements 124 into one or more sub-apertures.

The transducer elements 124 convert the received echo signals into electrical signals which may be received by a receiver 128. The receiver 128 may include one or more amplifiers, an analog to digital converter (ADC), and/or the like. The receiver 128 may be configured to amplify the received echo signals after proper gain compensation and convert these received analog signals from each transducer element 124 to digitized signals sampled uniformly in time. The digitized signals representing the received echoes are stored on memory 140, temporarily. The digitized signals correspond to the backscattered waves receives by each transducer element 124 at various times. After digitization, the signals still may preserve the amplitude, frequency, phase information of the backscatter waves.

Optionally, the controller circuit 136 may retrieve the digitized signals stored in the memory 140 to prepare for the beamformer processor 130. For example, the controller circuit 136 may convert the digitized signals to baseband signals or compressing the digitized signals.

The beamformer processor 130 may include one or more processors. Optionally, the beamformer processor 130 may include a central controller circuit (CPU), one or more microprocessors, or any other electronic component capable of processing inputted data according to specific logical instructions. Additionally, or alternatively, the beamformer processor 130 may execute instructions stored on a tangible and non-transitory computer readable medium (e.g., the memory 140) for beamforming calculations using any suitable beamforming method such as adaptive beamforming, synthetic transmit focus, aberration correction, synthetic aperture, clutter reduction and/or adaptive noise control, and/or the like.

The beamformer processor 130 may further perform filtering and decimation, such that only the digitized signals corresponding to relevant signal bandwidth is used, prior to beamforming of the digitized data. For example, the beamformer processor 130 may form packets of the digitized data based on scanning parameters corresponding to focal zones, expanding aperture, imaging mode (B-mode, color flow), and/or the like. The scanning parameters may define channels and time slots of the digitized data that may be beamformed, with the remaining channels or time slots of digitized data that may not be communicated for processing (e.g., discarded).

The beamformer processor 130 performs beamforming on the digitized signals and outputs a radio frequency (RF) signal. The RF signal is then provided to an RF processor 132 that processes the RF signal. The RF processor 132 may generate different ultrasound image data types, e.g. B-mode, for multiple scan planes or different scanning patterns. The RF processor 132 gathers the information (e.g. I/Q, B-mode) related to multiple data slices and stores the data information, which may include time stamp and orientation/rotation information, in the memory 140.

Alternatively, the RF processor 132 may include a complex demodulator (not shown) that demodulates the RF signal to form IQ data pairs representative of the echo signals. The RF or IQ signal data may then be provided directly to the memory 140 for storage (e.g., temporary storage). Optionally, the output of the beamformer processor 130 may be passed directly to the controller circuit 136.

The controller circuit 136 may be configured to process the acquired ultrasound data (e.g., RF signal data or IQ data pairs) and identify select sets and/or a portion of the ultrasound data within the ROI that corresponding to an anatomy of interest. The controller circuit 136 may include one or more processors. Optionally, the controller circuit 136 may include a central controller circuit (CPU), one or more microprocessors, a graphics controller circuit (GPU), or any other electronic component capable of processing inputted data according to specific logical instructions. Having the controller circuit 136 that includes a GPU may be advantageous for computation-intensive operations, such as volume-rendering. Additionally or alternatively, the controller circuit 136 may execute instructions stored on a tangible and non-transitory computer readable medium (e.g., the memory 140) to perform one or more operations as described herein.

The controller circuit 136 may be configured to acquire 3D ultrasound data of the volumetric ROI from the ultrasound probe 126. The controller circuit 136 may be configured to identify a select set of the 3D ultrasound data corresponding to the object of interest within the volumetric ROI. The controller circuit 136 may be configured to segment the object of interest from the select set of the 3D ultrasound data, generating a visualization plane of the object of interest, and display the visualization plane on the display 138.

The memory 140 may be used for storing ultrasound data such as vector data, processed frames of acquired ultrasound data that are not scheduled to be displayed immediately or to store post-processed images, firmware or software corresponding to, for example, a graphical user interface, one or more default image display settings, programmed instructions (e.g., for the controller circuit 136, the beamformer processor 130, the RF processor 132), and/or the like. The memory 140 may be a tangible and non-transitory computer readable medium such as flash memory, RAM, ROM, EEPROM, and/or the like.

In operation, the ultrasound data may include and/or correspond to three-dimensional (3D) ultrasound data. The memory 140 may store the 3D ultrasound data, where the 3D ultrasound data or select sets of the 3D ultrasound data are accessed by the controller circuit 136 to generate visualizations of the object of interest. For example, the 3D ultrasound data may be mapped into the corresponding memory 140, as well as one or more visualization planes based on the 3D ultrasound data. The processing of the 3D ultrasound data may be based in part on user inputs, for example, user selections received at the user interface 142.

The controller circuit 136 is operably coupled to a display 138 and a user interface 142. The display 138 may include one or more liquid crystal displays (e.g., light emitting diode (LED) backlight), organic light emitting diode (OLED) displays, plasma displays, CRT displays, and/or the like. The display 138 may display patient information, ultrasound images and/or videos, components of a display interface, one or more 2D, 3D, or 4D ultrasound image data sets from ultrasound data stored in the memory 140, measurements, diagnosis, treatment information, and/or the like received by the display 138 from the controller circuit 136.

The user interface 142 controls operations of the controller circuit 136 and is configured to receive inputs from the user. The user interface 142 may include a keyboard, a mouse, a touchpad, one or more physical buttons, and/or the like. Optionally, the display 138 may be a touch screen display, which includes at least a portion of the user interface 142.

For example, a portion of the user interface 142 may correspond to a graphical user interface (GUI) generated by the controller circuit 136, which is shown on the display. The GUI may include one or more interface components that may be selected, manipulated, and/or activated by the user operating the user interface 142 (e.g., touch screen, keyboard, mouse). The interface components may be presented in varying shapes and colors, such as a graphical or selectable icon, a slide bar, a cursor, and/or the like. Optionally, one or more interface components may include text or symbols, such as a drop-down menu, a toolbar, a menu bar, a title bar, a window (e.g., a pop-up window) and/or the like. Additionally or alternatively, one or more interface components may indicate areas within the GUI for entering or editing information (e.g., patient information, user information, diagnostic information), such as a text box, a text field, and/or the like.

In various embodiments, the interface components may perform various functions when selected, such as measurement functions, editing functions, database access/search functions, diagnostic functions, controlling acquisition settings, and/or system settings for the ultrasound imaging system 100 and performed by the controller circuit 136.

Figure 2:
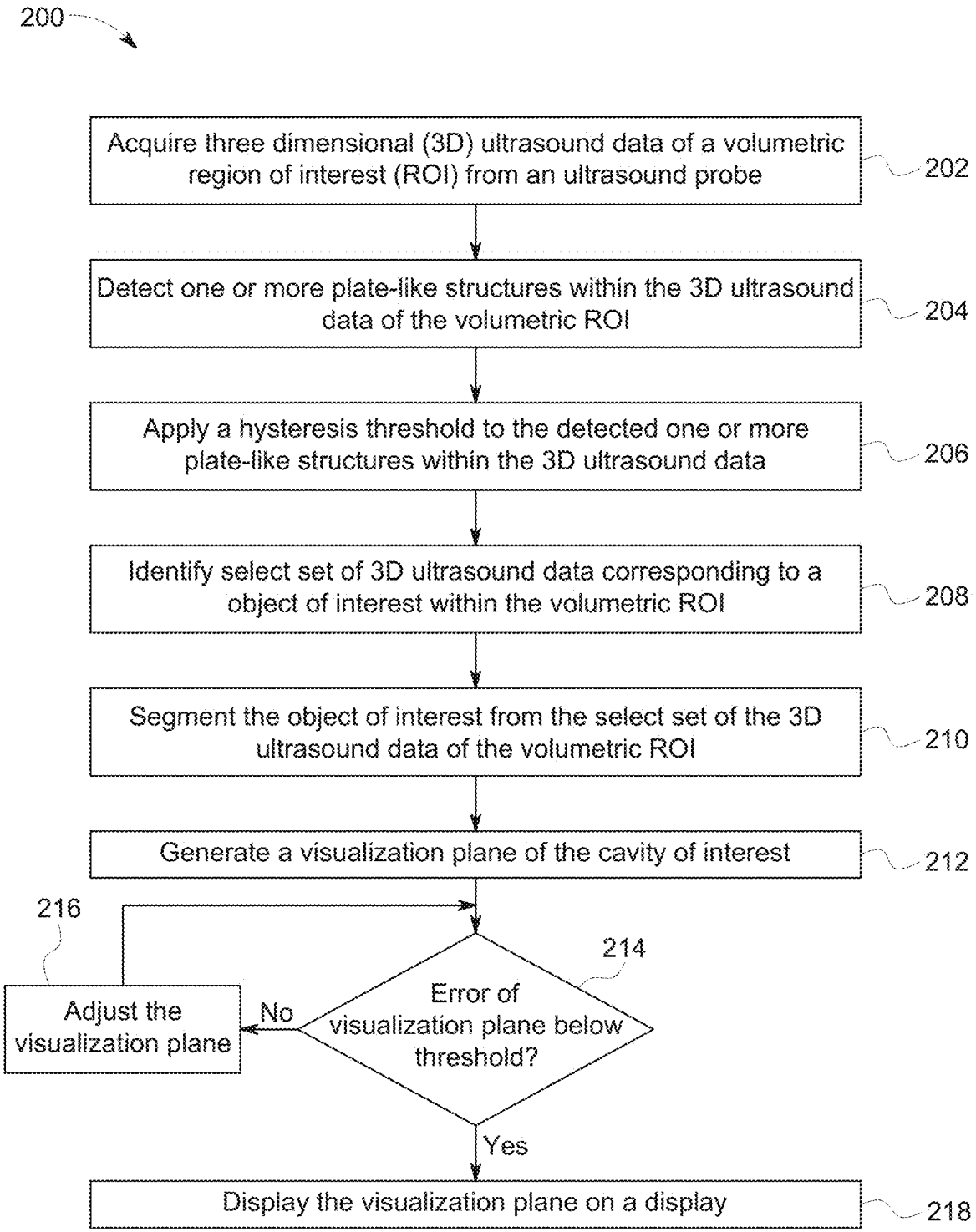
FIG. 2 illustrate a flowchart of a method for generating a visualization plane, in accordance with an embodiment.

In connection with FIG. 2, the user may select an interface component corresponding to a select scan, which generates a visualization plane of an object of interest using the user interface 142. When the interface component is selected, the controller circuit 136 may perform one or more of the operations described in connection with method 200. For example, the select scan may correspond to a uterine examination to detect anomalies. During the selected scan, the controller circuit may automatically extract the object of interest, such as an endometrium cavity, from 3D ultrasound data of a volumetric ROI and visualize the object of interest three-dimensionally and/or rendered along a visualization plane (e.g., mid-coronal) of the object of interest.

FIG. 2 a flowchart of a method 200 for generating a visualization plane, in accordance with an embodiment. The method 200, for example, may employ structures or aspects of various embodiments (e.g., systems and/or methods) discussed herein. In various embodiments, certain steps (or operations) may be omitted or added, certain steps may be combined, certain steps may be performed simultaneously, certain steps may be performed concurrently, certain steps may be split into multiple steps, certain steps may be performed in a different order, or certain steps or series of steps may be re-performed in an iterative fashion. In various embodiments, portions, aspects, and/or variations of the method 200 may be used as one or more algorithms to direct hardware to perform one or more operations described herein. It may be noted, other methods may be used, in accordance with embodiments herein.

Beginning at 202, the controller circuit 136 acquires 3D ultrasound data of a volumetric region of interest (ROI) from an ultrasound probe 126. For example, during acquisition the ultrasound probe 126 may be positioned and/or traverse at one or more select positions on and/or within the patient corresponding to a volumetric ROI. Optionally, the controller circuit 136 may automatically adjust the acquisition settings of the ultrasound probe 126 based on the volumetric ROI. For example, the predetermined scan (e.g., uterine scan) may be done transvaginally within the patient 402, which positions the ultrasound probe 126 within the object of interest, such as a cavity. The controller circuit 136 may adjust the acquisition settings, such as the amplitude, pulse width, frequency and/or the like of the ultrasound pulses emitted by the transducer elements 124 of the ultrasound probe 126 based on being positioned within the object of interest.

Additionally, or alternatively, the controller circuit 136 may automatically instruct the ultrasound probe 126 to begin transmitting ultrasonic pulses based on a received input from the user interface 142 and/or activation of a tactile button on the ultrasound probe 126.

At least a portion of the ultrasound pulses are backscattered by the tissue of the volumetric ROI, and are received by the receiver 128. The receiver 128 converts the received echo signals into digitized signals. The digitized signals, as described herein, are beamformed by the beamformer processor 130 and formed into IQ data pairs representative of the echo signals by the RF processor 132, and are received as 3D ultrasound data by the controller circuit 136. The 3D ultrasound data may be processed by the controller circuit 136. For example, the controller circuit 136 may process the IQ data pairs to generate B-mode data, for example, sets of vector data values forming a frame of the 3D ultrasound data stored in the memory 140. Additionally, or alternatively, as the 3D ultrasound data is being acquired the display 138 may display a real-time 3D ultrasound image and/or an ultrasound image based on the 3D ultrasound data while simultaneously and/or concurrently acquiring 3D ultrasound data.

At 204, the controller circuit 136 detects one or more plate-like structures within the 3D ultrasound data of the volumetric ROI using a plate-like function. A plate-like structure may correspond to an interconnection of voxels of the 3D ultrasound data that form a portion of the object of interest along a 3D plane. The multiscale, eigenvalue decomposition is performed over a Hessian matrix and the resulting ordered eigenvalues (e.g., $\lambda_1, \lambda_2, \lambda_3$), are examined by the controller circuit 136. The controller circuit 136 may detect a plurality of plate-like structures within the 3D ultrasound data by executing a Hessian response algorithm stored in the memory 104 based on Equation 1. By utilizing Equation 1, the controller circuit 136 measures a plate-like (represented as the variable $P_o$) of a plurality of voxels using eigenvalues of the Hessian matrix of the 3D ultrasound data. For example, the controller circuit 136 may identify a plate-like structure formed by relative positions of a plurality of voxels within the 3D ultrasound data. The variables a and c correspond to user defined and/or predetermined parameters based on the object of interest and/or volumetric ROI. The number of voxels included within the plate-like calculation is based on a scale, represented as a. The scale may correspond to a thickness of the voxels selected by the controller circuit 136 to determine the plate-like structures within the 3D ultrasound data. The scale may be a predetermined value stored in the memory 104, user selection, and/or the like based on a size of the object of interest. Additionally or alternatively, the controller circuit 136 may calculate the plate-like structures within the 3D ultrasound data at different scales.

$$P_\sigma(x) = \left(1 - e^{-\frac{\sum \lambda_j^2}{2c^2}}\right)\left(1 - e^{-\frac{\sqrt{|\lambda_3|(|\lambda_3| - |\lambda_2|)}}{2a^2}}\right) \quad \text{Equation (1)}$$

At 206, the controller circuit 136 applies dynamic hysteresis thresholds to the detected plate-like structures within the 3D ultrasound data. The controller circuit 136 is configured to calculate a dynamic hysteresis threshold for each of the detected plate-like structures. The dynamic hysteresis threshold is configured by the controller circuit 136 to differentiate voxels that correspond to anatomical structures of interest (e.g., the object of interest) within the detected plate-like structures. The dynamic hysteresis threshold corresponds to a dynamic value calculated by the controller circuit 136 based on corresponding histograms calculated from each of the detected plate-like structures. For example, the controller circuit 136 calculates a first and second hysteresis threshold for detected plate-like structures based on the histogram of the detected plate-like structures. The histograms may be derived by the controller circuit 136 from the voxel intensities along the detected plate-like structure. It may be noted that the histograms and the dynamic hysteresis threshold may be different for at least two of the detected plate-like structures of the 3D ultrasound data. For example, the first and second hysteresis threshold may be different.

Figure 3:
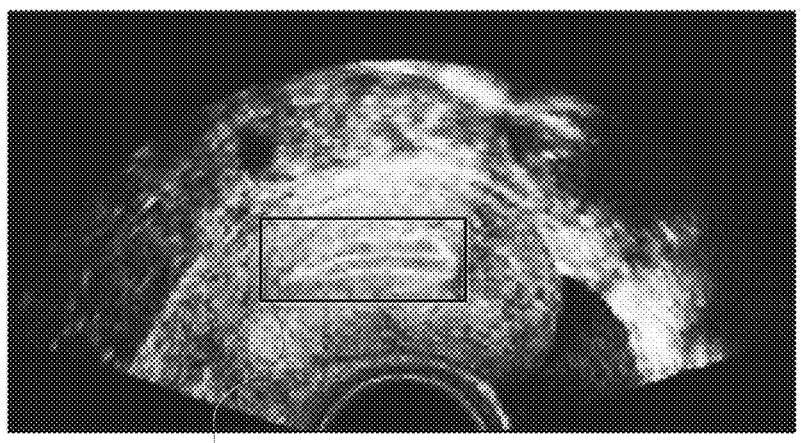
FIG. 3 illustrates a detected plate-like structure of 3D ultrasound data, in accordance with an embodiment.
Figure 4:
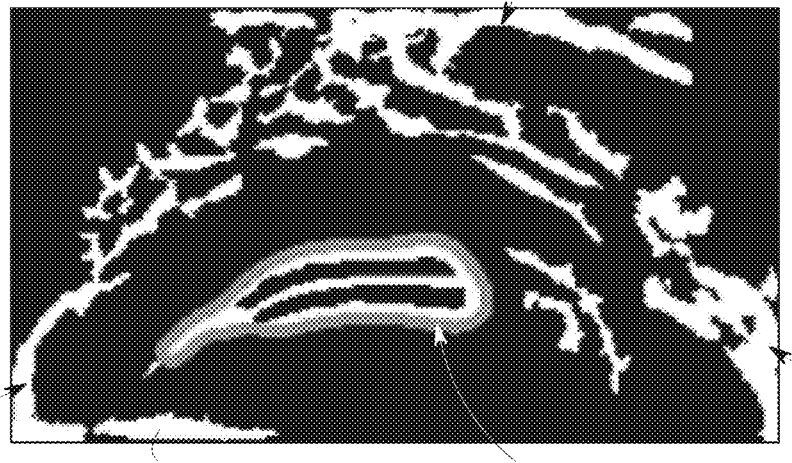
FIG. 4 illustrates an adjusted detected plate-like structure, in accordance with an embodiment.

In connection with FIGS. 3-4, the controller circuit 136 applies the dynamic hysteresis threshold to the voxels of a detected plate-like structure 302 to generate an adjusted detected plate-like structure 400 having binary voxel intensities.

FIG. 3 illustrates the detected plate-like structure 302 of the 3D ultrasound data 300, in accordance with an embodiment. The detected plate-like structure 302 includes voxels have varying levels of intensity representing anatomical structures within the 3D ultrasound data 300 of the volumetric ROI such as the object of interest, background anatomical structure, and/or the like. The controller circuit 136 is configured to apply the dynamic hysteresis thresholds calculated from the detected plate-like structure 302 to the voxels of the detected plate-like structure 302. For example, the controller circuit 136 partitions the detected plate-like structure 302 into three separate regions. Region 1 is configured to contain all voxels with intensity values below a first hysteresis threshold. Region 1 represents the foreground region containing the anatomical structures of interest (e.g., the object of interest). Region 2 is configured to contain all voxels with intensity values between the first hysteresis threshold and a second hysteresis threshold. Region 3 is configured to contain all voxels with intensity values above the second hysteresis threshold. Region 2 represents an intermediate region and region 3 represents background anatomical structures. Each voxel in region 2 is analyzed by the controller circuit 136 based on adjacent and/or neighboring voxels. For example, if a select voxel belonging to region 2 has a neighbor in region 1, then the controller circuit 136 is configured to re-assign the select voxel to region 1. The controller circuit 136 may repeat the process for each voxel within region 2. The remaining voxels in region 2 may be assigned to region 3. Each voxel belonging to region 1 is then assigned by the controller circuit 136 to a high binary intensity and each voxel belonging to region 3 is assigned a low binary intensity.

The adjusted voxels of the detect plate-like structure 302 by the controller circuit 136 generates an adjusted detected plate-like structure 400 shown in FIG. 4.

FIG. 4 illustrates the adjusted detected plate-like structure 400. The adjusted detected plate-like structure 400 is formed by voxels having binary intensities (e.g., high, low) based on the detected plate-like structure 302 and the dynamic hysteresis threshold. For example, the high intensity voxels may correspond to portions of the detected plate-like structure 302 of an anatomical structure of interest (e.g., the object of interest) corresponding to region 1, and the low intensity voxels may correspond to portions of the detected plate-like structure 302 not of an anatomical structure of interest corresponding to region 3.

At 208, the controller circuit 136 identifies a select set of 3D ultrasound data corresponding to an object of interest within the volumetric ROI. The controller circuit 136 may identify the select set of 3D ultrasound data by identifying the voxels of the detected plate-like structures that correspond to the object of interest.

For example, the controller circuit 136 may detect the locations of the high intensity voxels within the adjusted detected plate-like structure 400. Based on the continuity, shapes, contours, relative positions, and/or the like of the high intensity voxels, the controller circuit 136 may identify one or more anatomical structures of interest 402-405. The controller circuit 136 may utilize a machine learning algorithm stored in the memory 104 to identify the object of interest (e.g., endometrium cavity) based on characteristics of the anatomical structure of interest 402-405 identified within the adjusted detected plate-like structure 400. For example, the controller circuit 136 may compare a vertical position, orientation, convex area, angular displacement, and/or the like of the anatomical structures of interests 402-405 to identify which corresponds to the object of interest. The machine learning algorithm may be defined using classifiers (e.g., random forest classifier), probabilities (e.g., Bayesian generative learning), and/or the like based on priori information. For example, the priori information may include a plurality of clinical examples (e.g., over 150) of the object of interest within the 3D ultrasound data stored in the memory 140.

In various embodiments, the controller circuit 136 may calculate probabilities of the anatomical structures of interests 402-405 being the object of interest utilizing the machine learning algorithm. The controller circuit 136 may select one of the anatomical structures of interest 402-405 that has the highest probability relative to the remaining probabilities of the anatomical structures of interest 402-405. For example, the controller circuit 136 may select the anatomical structure of interest 402 as the object of interest since the probability corresponding to the anatomical structures of interest 402 was higher relative to the probabilities of the remaining anatomical structures in the background 403-405. The controller circuit 136 may include the voxels of the structure of interest 402 to a select set of the 3D ultrasound data from the volumetric ROI.

Additionally, or alternatively, the controller circuit 136 may select one or more candidate anatomical structures of interest that have a probability over a predetermined threshold. For example, the controller circuit 136 may instruct the display 138 to display the candidate anatomical structures of interest, and receive a user input from the user interface 142 indicative of a selection of one of the candidate anatomical structure of interest as the object of interest.

Returning to FIG. 2, at 210 the controller circuit 136 segments the object of interest from the select set of the 3D ultrasound data from the volumetric ROI. For example, the controller circuit 136 may execute an active contour model (e.g., geometric deformable model, snake, and/or the like) to define a boundary of the select set of the 3D ultrasound data with respect to the volumetric ROI. The controller circuit 136, in connection with FIG. 5, partitions the select set of the 3D ultrasound data to form an object of interest 502.

Figure 5:
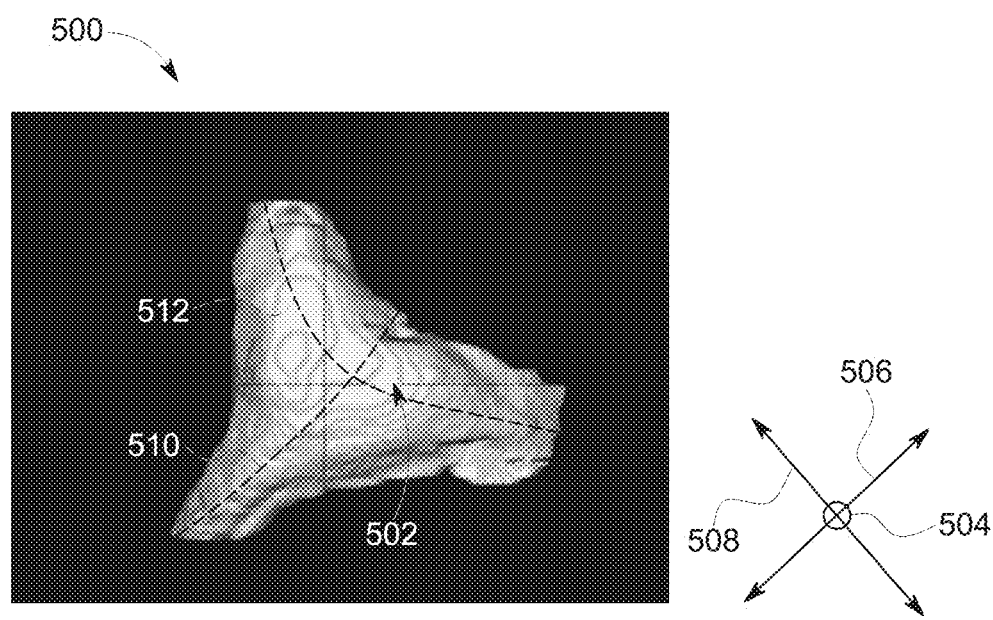
FIG. 5 illustrates a segmentation of an object of interest, in accordance with an embodiment.

FIG. 5 illustrates a segmentation 500 of the object of interest 502. For example, the object of interest 502 is formed by the select set of the 3D ultrasound data and may be displayed on the display 138. Optionally, the controller circuit 136 may adjust a position and/or angle of the object of interest 502. For example, the controller circuit 136 may adjust a position by rotating the object of interest 502 about one or more axes of rotation 504, 506, 508 based on a user input received by the user interface 142. Additionally, or alternatively, the controller circuit 136 may execute a texture mapping (e.g., diffuse mapping) algorithm to add additional details to a surface area, topology, and/or the like of the object of interest 502.

At 212, the controller circuit 136 may generate a visualization plane 604 of the object of interest 502. The visualization plane 604 (FIGS. 6A-B) can extend along axes 510, 512 (FIG. 5) of the object of interest 502. The visualization plane 604 may correspond to a hypersurface of the object of interest 502. For example, the object of interest 502 is utilized by the controller circuit 136 as a 3D manifold utilized to define the hypersurface representing the visualization plane 604. In connection with FIGS. 6A-B, the controller circuit 136 may generate the visualization plane 604 based on a surface fitting of the visualization plane 604 to the object of interest 502.

Figure 6A:
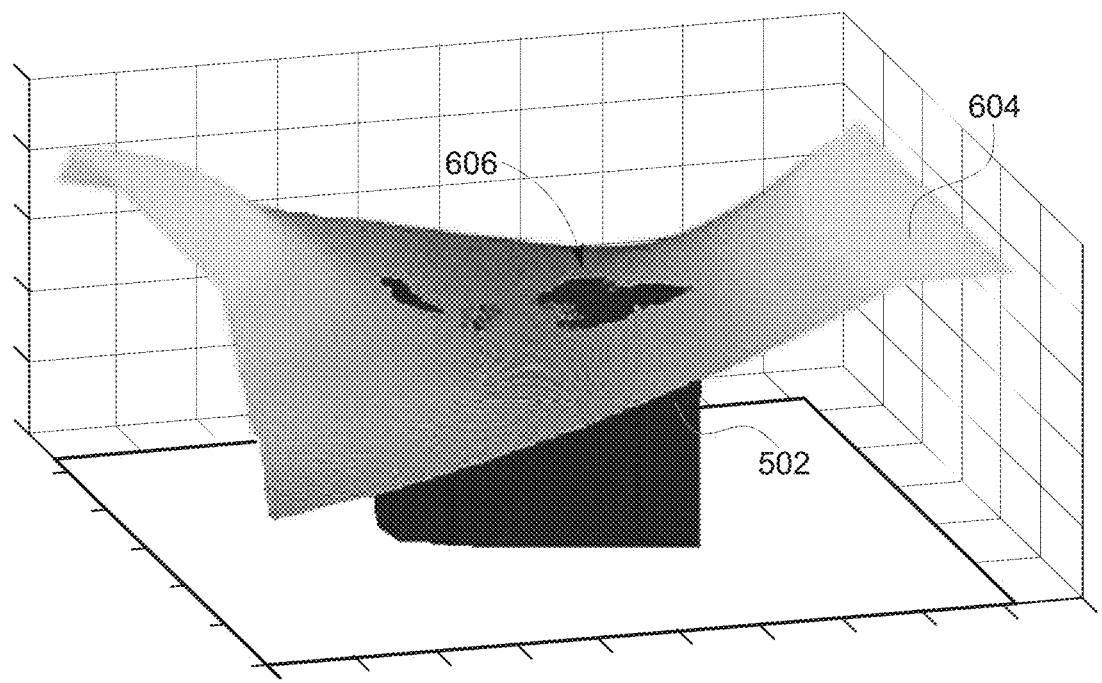
FIG. 6A-B illustrates a visualization plane with respect to the segmentation of the object of interest shown in FIG. 5, in accordance with an embodiment.
Figure 6B:
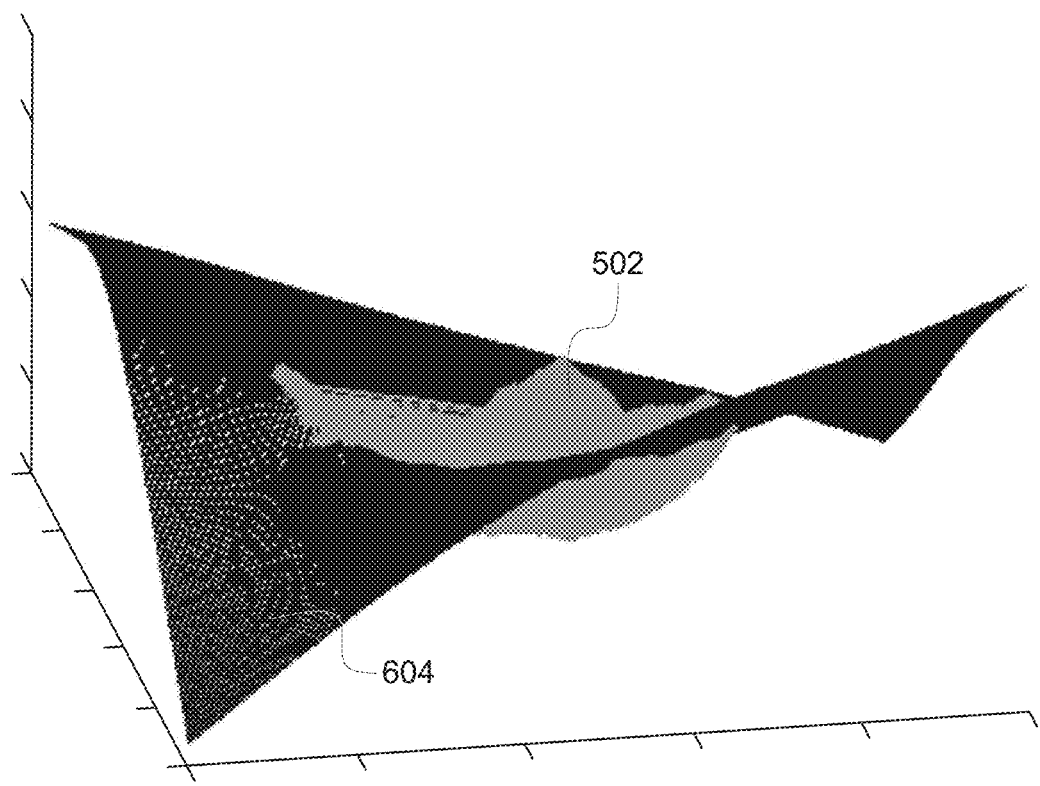

FIG. 6A-B illustrates the visualization plane 604 with respect to the segmentation of the object of interest 502, in accordance with an embodiment. The controller circuit 136 may calculate a polynomial (e.g., Legendre polynomial) representative of the object of interest 502, which is extrapolated by the controller circuit 136 outside the surface area 606. For example, in connection with FIG. 6A, the controller circuit 136 calculates a polynomial based on surface area 606 of the object of interest. In connection with FIG. 6B, the controller circuit 136 may generate the visualization plane 604 at different positions within the object of interest 502. For example, the object of interest 502 may be an endometrium cavity. The controller circuit 136 may calculate a polynomial (e.g., Legendre polynomial) along the visualization plane 604 interposed within the object of interest 502 to configure the visualization plane 604 to represent a mid-coronal plane of the object of interest 502.

At 214, the controller circuit 136 determines whether an error of the visualization plane 604 is below an error threshold. For example, the controller circuit 136 may execute a least square regularizer (e.g., least square energy minimization) to adjust the polynomial calculated at 212. The controller circuit 136 may determine an error between the visualization plane 604 and the object of interest 502.

If the error is not below the error threshold, then at 216 the controller circuit 136 may adjust the visualization plane 604. For example, the controller circuit 136 may continually adjust the polynomial defining the visualization plane 604 at 212, 214, and 216 to adjust the visualization plane 604 with respect to the object of interest 502 until the error is below the error threshold.

If the error is below the error threshold, then at 218 the controller circuit 136 may display the visualization plane 604 on the display 138. In connection with FIG. 7, the controller circuit 136 may instruct the display 138 to display the visualization plane 604. Optionally, the controller circuit 136 may adjust a rotational position of the visualization plane 604. In connection with FIGS. 8-9, the controller circuit 136 may adjust a rotational position and/or view of the visualization plane 604 by adjusting the visualization plane 604 with respect to one or more axes 702, 704, 706 based on a user input received by the user interface 142. The axes 702, 704, 706 may represent three orthogonal planes corresponding to a mid-coronal plane, a mid-sagittal plane, and a mid-axial plane.

Additionally, or alternatively, the controller circuit 136 may display the visualization plane 604 as a plurality of two-dimensional (2D) slices. For example, the controller circuit 136 may receive a user input from the user interface 142 to adjust the visualization plane 604. Based on the user input, the controller circuit 136 may automatically partition the visualization plane 604 into a plurality of 2D slices. Optionally, the controller circuit 136 may be configured to arrange the plurality of 2D slices as a polyline representative of the visualization plane 604. The controller circuit 136 may receive one or more user inputs indicative of an adjustment to a position and/or orientation of at least one of the 2D slices. Based on the change in position and/or orientation, the controller circuit 136 may be configured to adjust the visualization plane 604.

Figure 7:
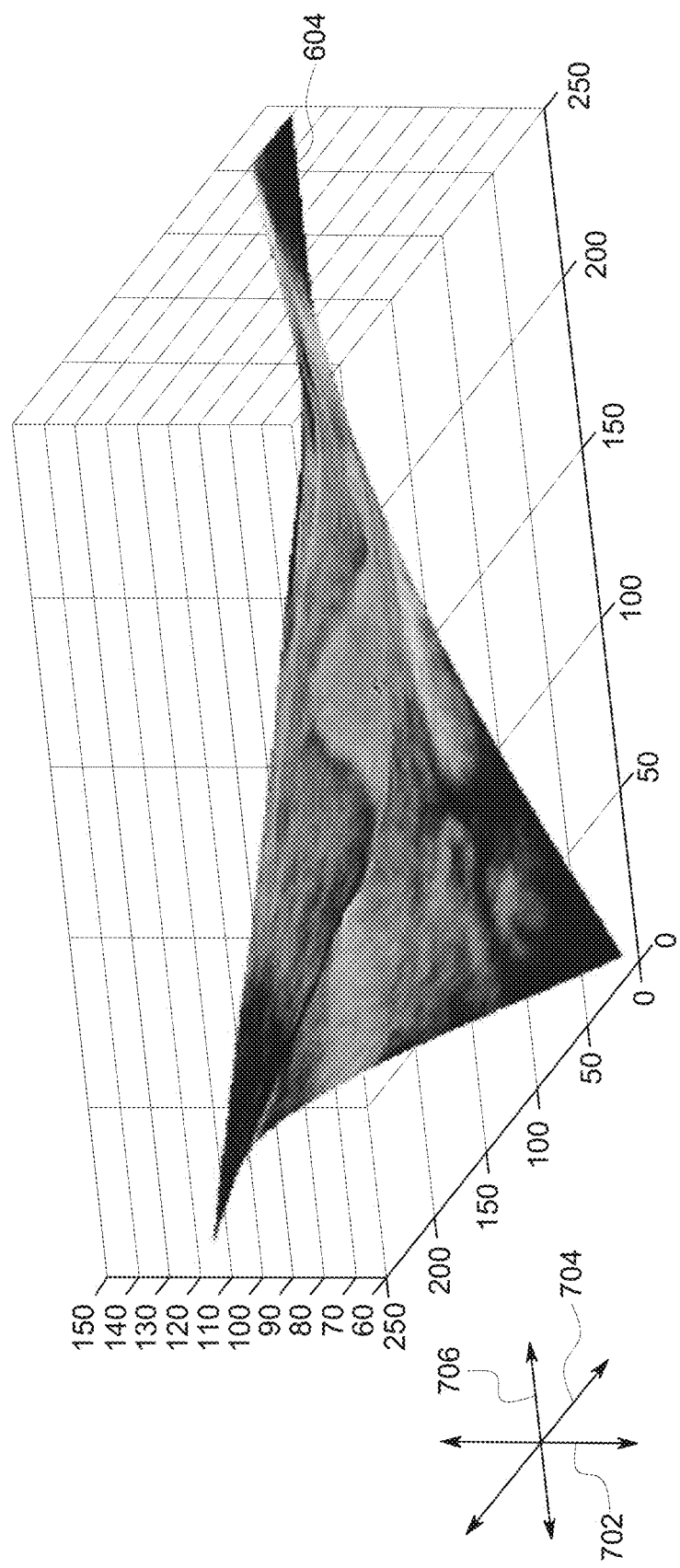
FIG. 7 illustrates a visualization plane, in accordance with an embodiment.
Figure 8:
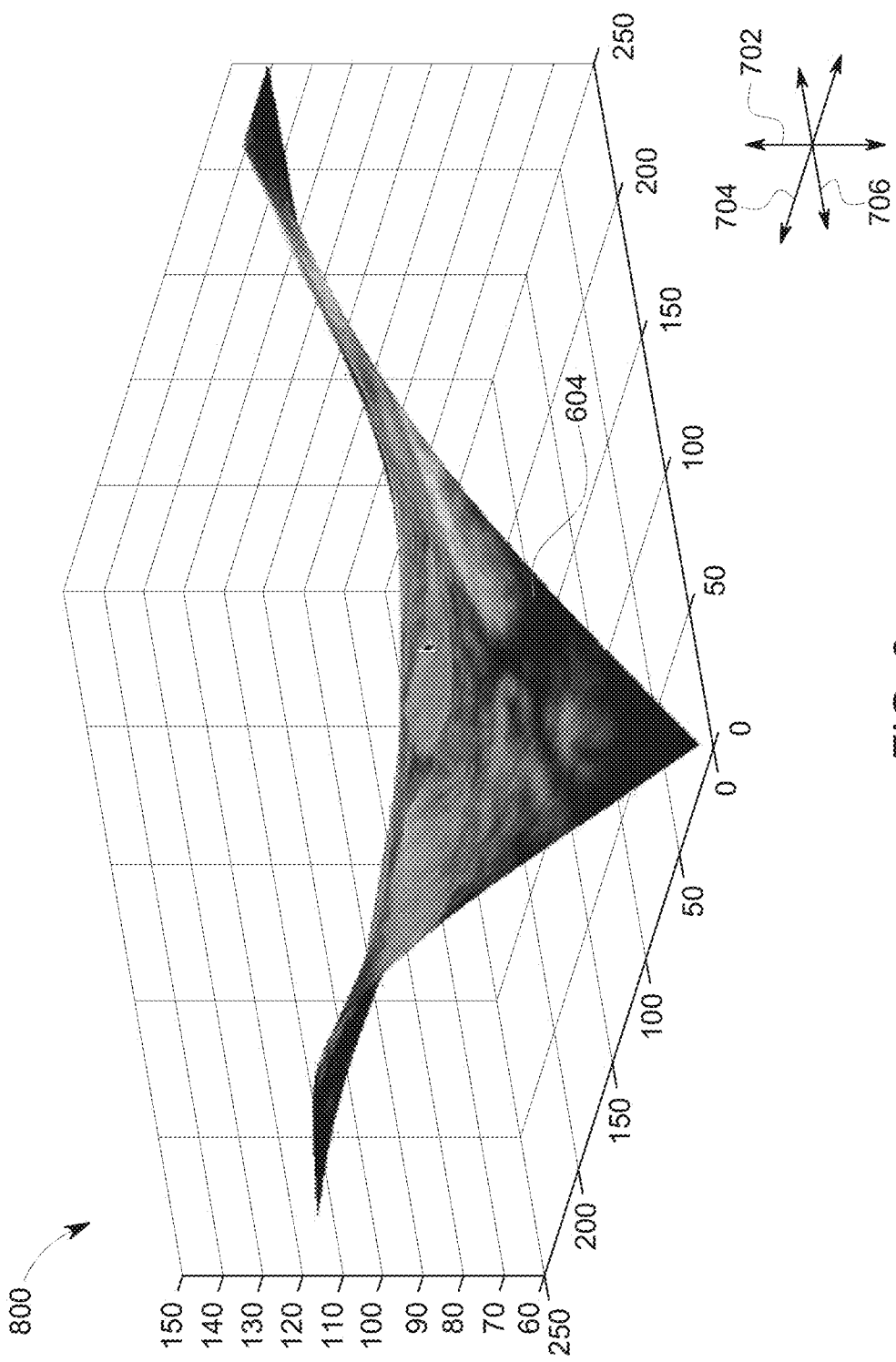
FIGS. 8-9 illustrate different rotations of the visualization plane shown in FIG. 7, in accordance with an embodiment.

FIG. 8 illustrates a different rotation 800 of the of the visualization plane 604 relative to the visualization plane 604 shown in FIG. 7. For example, the controller circuit 136 may receive a user input indicative of rotating the visualization plane 604 about the axis of rotation 702.

Figure 9:
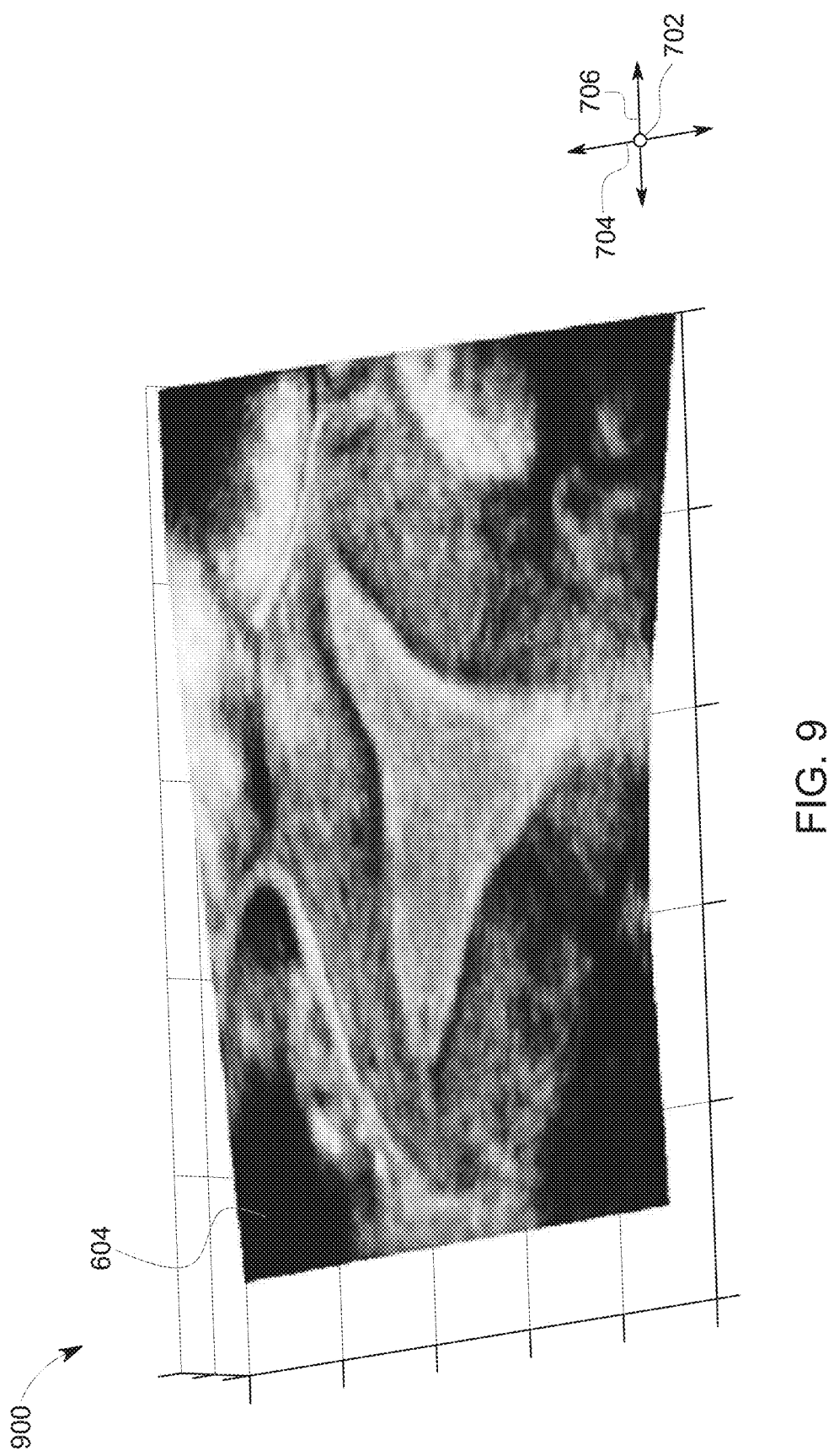

FIG. 9 illustrates a different rotation 900 of the of the visualization plane 604 relative to the visualization plane 604 shown in FIGS. 7-8. For example, the controller circuit 136 may receive a user input indicative of rotating the visualization plane 604 about the axis of rotation 706.

Additionally, or alternatively, the visualization plane 604 may include multiple surfaces fit on the object of interest 502. Each surface is projected along three orthogonal 2D planes. Each of the 2D planes may represent one of the orthogonal planes corresponding to the axes 702, 704, and 706. Optionally, the 2D planes may represent a mid-coronal plane, a mid-sagittal plane, and/or a mid-axial plane.

Figure 10:
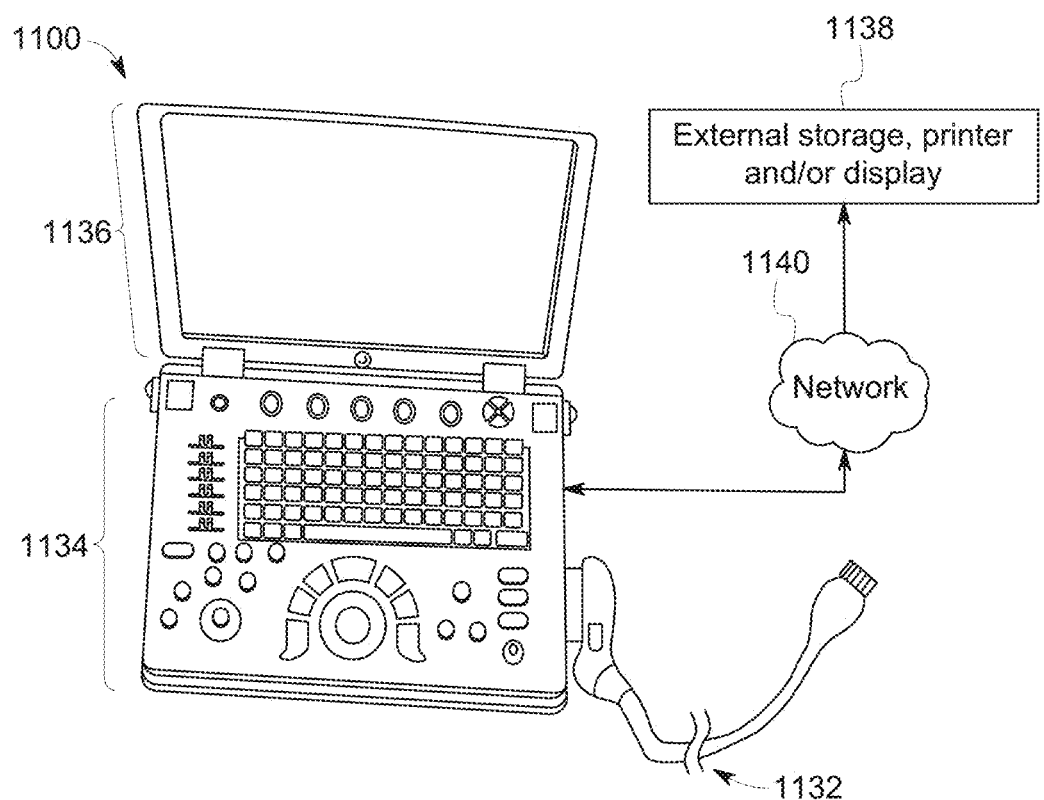
FIG. 10 illustrates a 3D capable miniaturized ultrasound system having a probe that may be configured to acquire 3D ultrasonic data or multi-plane ultrasonic data.
Figure 11:
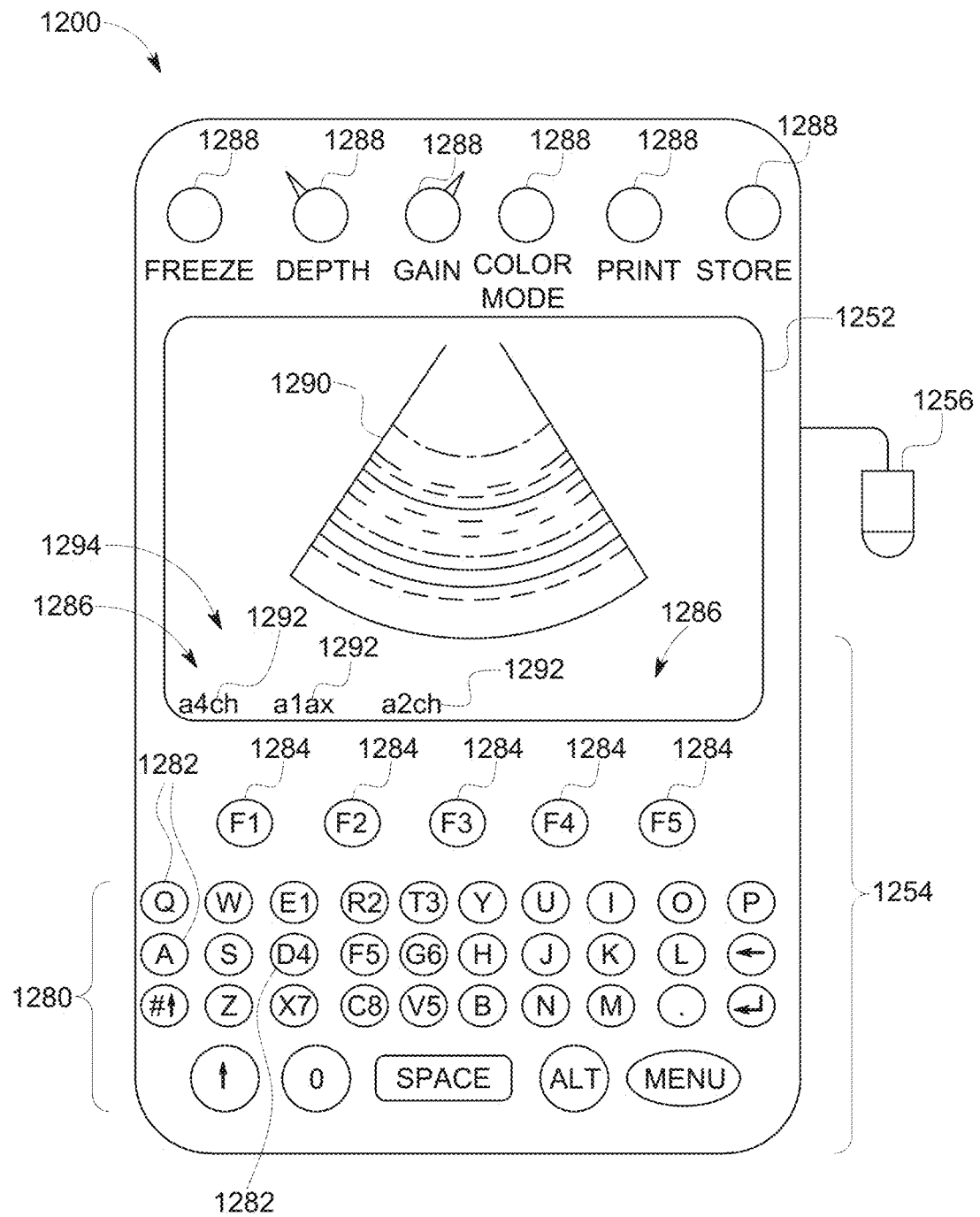
FIG. 11 illustrates a hand carried or pocket-sized ultrasound imaging system wherein the display and user interface form a single unit.
Figure 12:
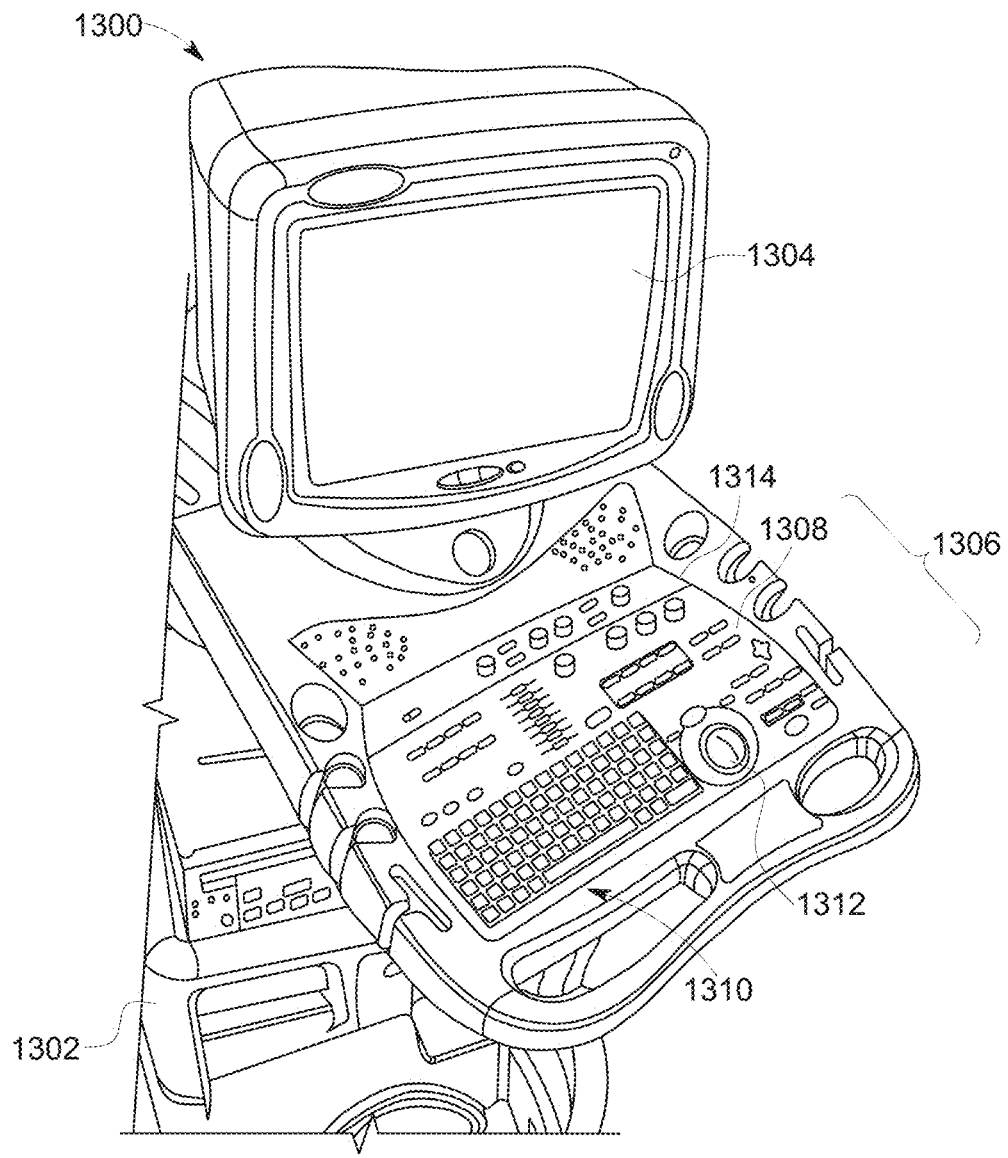
FIG. 12 illustrates an ultrasound imaging system provided on a movable base.

The ultrasound imaging system 100 of FIG. 1 may be embodied in a small-sized system, such as laptop computer or pocket-sized system as well as in a larger console-type system. FIGS. 10 and 11 illustrate small-sized systems, while FIG. 12 illustrates a larger system.

FIG. 10 illustrates a 3D-capable miniaturized ultrasound system 1130 having a probe 1132 that may be configured to acquire 3D ultrasonic data or multi-plane ultrasonic data. For example, the probe 1132 may have a 2D array of elements as discussed previously with respect to the probe. A user interface 1134 (that may also include an integrated display 1136) is provided to receive commands from an operator. As used herein, "miniaturized" means that the ultrasound system 1130 is a handheld or hand-carried device or is configured to be carried in a person's hand, pocket, briefcase-sized case, or backpack. For example, the ultrasound system 1130 may be a hand-carried device having a size of a typical laptop computer. The ultrasound system 1130 is easily portable by the operator. The integrated display 1136 (e.g., an internal display) is configured to display, for example, one or more medical images.

The ultrasonic data may be sent to an external device 1138 via a wired or wireless network 1140 (or direct connection, for example, via a serial or parallel cable or USB port). In some embodiments, the external device 1138 may be a computer or a workstation having a display. Alternatively, the external device 1138 may be a separate external display or a printer capable of receiving image data from the hand carried ultrasound system 1130 and of displaying or printing images that may have greater resolution than the integrated display 1136.

FIG. 11 illustrates a hand carried or pocket-sized ultrasound imaging system 1200 wherein the display 1252 and user interface 1254 form a single unit. By way of example, the pocket-sized ultrasound imaging system 1200 may be a pocket-sized or hand-sized ultrasound system approximately 2 inches wide, approximately 4 inches in length, and approximately 0.5 inches in depth and weighs less than 3 ounces. The pocket-sized ultrasound imaging system 1200 generally includes the display 1252, user interface 1254, which may or may not include a keyboard-type interface and an input/output (I/O) port for connection to a scanning device, for example, an ultrasound probe 1256. The display 1252 may be, for example, a 320×320 pixel color LCD display (on which a medical image 1290 may be displayed). A typewriter-like keyboard 1280 of buttons 1282 may optionally be included in the user interface 1254.

Multi-function controls 1284 may each be assigned functions in accordance with the mode of system operation (e.g., displaying different views). Therefore, each of the multi-function controls 1284 may be configured to provide a plurality of different actions. One or more interface components, such as label display areas 1286 associated with the multi-function controls 1284 may be included as necessary on the display 1252. The system 1200 may also have additional keys and/or controls 1288 for special purpose functions, which may include, but are not limited to "freeze," "depth control," "gain control," "color-mode," "print," and "store."

One or more of the label display areas 1286 may include labels 1292 to indicate the view being displayed or allow a user to select a different view of the imaged object to display. The selection of different views also may be provided through the associated multi-function control 1284. The display 1252 may also have one or more interface components corresponding to a textual display area 1294 for displaying information relating to the displayed image view (e.g., a label associated with the displayed image).

It may be noted that the various embodiments may be implemented in connection with miniaturized or small-sized ultrasound systems having different dimensions, weights, and power consumption. For example, the pocket-sized ultrasound imaging system 1200 and the miniaturized ultrasound system 1130 may provide the same scanning and processing functionality as the system 100.

FIG. 12 illustrates an ultrasound imaging system 1300 provided on a movable base 1302. The portable ultrasound imaging system 1300 may also be referred to as a cart-based system. A display 1304 and user interface 1306 are provided and it should be understood that the display 1304 may be separate or separable from the user interface 1306. The user interface 1306 may optionally be a touchscreen, allowing the operator to select options by touching displayed graphics, icons, and the like.

The user interface 1306 also includes control buttons 1308 that may be used to control the portable ultrasound imaging system 1300 as desired or needed, and/or as typically provided. The user interface 1306 provides multiple interface options that the user may physically manipulate to interact with ultrasound data and other data that may be displayed, as well as to input information and set and change scanning parameters and viewing angles, and/or the like. For example, a keyboard 1310, trackball 1312 and/or multi-function controls 1314 may be provided.

It may be noted that the various embodiments may be implemented in hardware, software or a combination thereof. The various embodiments and/or components, for example, the modules, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as a solid-state drive, optical disk drive, and the like. The storage device may also be other similar means for loading computer programs or other instructions into the computer or processor.

As used herein, the term "computer," "subsystem" or "module" may include any processor-based or microprocessor-based system including systems using microcontrollers, reduced instruction set computers (RISC), ASICs, logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program. The software may be in various forms such as system software or application software and which may be embodied as a tangible and non-transitory computer readable medium. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein. Instead, the use of "configured to" as used herein denotes structural adaptations or characteristics, and denotes structural requirements of any structure, limitation, or element that is described as being "configured to" perform the task or operation. For example, a controller circuit, processor, or computer that is "configured to" perform a task or operation may be understood as being particularly structured to perform the task or operation (e.g., having one or more programs or instructions stored thereon or used in conjunction therewith tailored or intended to perform the task or operation, and/or having an arrangement of processing circuitry tailored or intended to perform the task or operation). For the purposes of clarity and the avoidance of doubt, a general purpose computer (which may become "configured to" perform the task or operation if appropriately programmed) is not "configured to" perform a task or operation unless or until specifically programmed or structurally modified to perform the task or operation.

As used herein, the terms "software" and "firmware" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing from their scope. While the dimensions and types of materials described herein are intended to define the parameters of the various embodiments, they are by no means limiting and are merely exemplary. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or the examples include equivalent structural elements with insubstantial differences from the literal language of the claims.

What is claimed is:

1. A method for determining a malformation of a uterus, the method comprising:
    acquiring three-dimensional (3D) ultrasound data of a volumetric region of interest (ROI) with an ultrasound probe, wherein the volumetric ROI includes at least a portion of the uterus;
    identifying a select set of the 3D ultrasound data corresponding to an object of interest within the volumetric ROI;
    segmenting the object of interest from the select set of the 3D ultrasound data;
    generating a visualization plane of the object of interest based on a fitting of the visualization plane to the object of interest, wherein the visualization plane corresponds to a hypersurface of the object of interest, and wherein the visualization plane is curved in at least two different directions to correspond to the hypersurface of the object of interest; and
    displaying the visualization plane on a display.

2. The method of claim 1, wherein the object of interest is a uterine cavity.

3. The method of claim 1, wherein the object of interest is an endometrial cavity.

4. The method of claim 1, further comprising calculating a polynomial along the visualization plane interposed within the object of interest to configure the object of interest to represent a mid-coronal plane of the object of interest.

5. The method of claim 4, wherein the polynomial is a Legendre polynomial.

6. The method of claim 1, wherein the visualization plane is projected along three orthogonal two-dimensional (2D) planes.

7. The method of claim 6, wherein one of the 2D planes correspond to a mid-coronal plane, a mid-sagittal plane, or a mid-axial plane.

8. The method of claim 1, wherein the visualization plane is displayed as a plurality of two-dimensional (2D) slices, and further comprising arranging the 2D slices as a polyline.

9. The method of claim 8, further comprising receiving a user input indicative of adjusting an orientation of at least one of the 2D slices, and adjusting the visualization plane based on the orientation of the at least one of the 2D slices.

10. The method of claim 1, wherein the select set of the 3D ultrasound data is identified utilizing a machine learning algorithm.

11. The method of claim 1, further comprising:
    receiving a user input indicative of a rotation of the visualization plane about a rotational axis;
    adjusting the visualization plane of the object of interest based on the rotation to form an adjusted visualization plane; and
    displaying the adjusted visualization plane on the display.

12. The method of claim 1, wherein the fitting is a surface fitting.

13. An ultrasound imaging system comprising:
    an ultrasound probe configured to acquire three-dimensional (3D) ultrasound data of a volumetric region of interest (ROI);
    a display;
    a memory configured to store programmed instructions; and
    a controller circuit having one or more processors, the controller circuit is configured to execute the programmed instructions stored in the memory, wherein the controller circuit when executing the programmed instructions performs the following operations:
    collect the 3D ultrasound data from an ultrasound probe of the volumetric ROI, wherein the volumetric ROI includes at least a portion of a uterus;
    identify a select set of the 3D ultrasound data corresponding to an object of interest within the volumetric ROI;
    segment the object of interest from the select set of the 3D ultrasound data;
    generate a visualization plane of the object of interest based on a fitting of the visualization plane to the object of interest, wherein the visualization plane corresponds to a hypersurface of the object of interest, and wherein the visualization plane is curved in at least two different directions to correspond to the hypersurface of the object of interest; and
    display the visualization plane on the display.

14. The ultrasound imaging system of claim 13, wherein the object of interest is a uterine cavity.

15. The ultrasound imaging system of claim 13, wherein the object of interest is an endometrial cavity.

16. The ultrasound imaging system of claim 13, wherein the controller circuit is configured to use the object of interest as a 3D manifold to define the hypersurface.

17. The ultrasound imaging system of claim 13, wherein the fitting is a surface fitting.

18. A tangible and non-transitory computer readable medium comprising one or more computer software modules configured to direct one or more processors to:
    acquire three-dimensional (3D) ultrasound data of a volumetric region of interest (ROI) from an ultrasound probe, wherein the volumetric ROI includes at least a portion of a uterus;
    identify a select set of the 3D ultrasound data corresponding to an object of interest within the volumetric ROI;
    segment the object of interest from the select set of the 3D ultrasound data;
    generate a visualization plane of the object of interest based on a fitting of the visualization plane to the object of interest, wherein the visualization plane corresponds to a hypersurface of the object of interest, and wherein the visualization plane is curved in at least two different directions to correspond to the hypersurface of the object of interest; and
    display the visualization plane on a display.

19. The tangible and non-transitory computer readable medium of claim 18, wherein the object of interest is a uterine cavity.

20. The tangible and non-transitory computer readable medium of claim 18, wherein the object of interest is an endometrial cavity.

* * * * *